United States Patent [19]

Loboda

[11] 4,129,496

[45] * Dec. 12, 1978

[54] HYDROCARBON REFORMING PROCESS

[75] Inventor: Robert S. Loboda, Hacienda Heights, Calif.

[73] Assignee: UOP Inc., Des Plaines, Ill.

[*] Notice: The portion of the term of this patent subsequent to May 15, 1994, has been disclaimed.

[21] Appl. No.: 823,794

[22] Filed: Aug. 11, 1977

Related U.S. Application Data

[63] Continuation-in-part of Ser. No. 706,858, Jul. 19, 1976, Pat. No. 4,058,452.

[51] Int. Cl.$^2$ ............................................ C10G 35/04
[52] U.S. Cl. ................................. 208/134; 260/672 R
[58] Field of Search .......................................... 208/134

[56] References Cited

U.S. PATENT DOCUMENTS 4,058,452  11/1977  Loboda ............................... 208/134

Primary Examiner—C. Davis
Attorney, Agent, or Firm—James R. Hoatson, Jr.; John F. Spears, Jr.; William H. Page, II

[57] ABSTRACT

A process for the catalytic reforming of hydrocarbons wherein a hydrogen-rich gas stream passed through the reaction zone on a once-through basis is obtained by passing a hydrogen-containing feed gas stream through an absorber which removes light paraffins. The gas separated from the reaction zone effluent by partial condensation is passed into a stripper as the stripping media used to remove these same light paraffins from the liquid used in the absorber.

2 Claims, 1 Drawing Figure

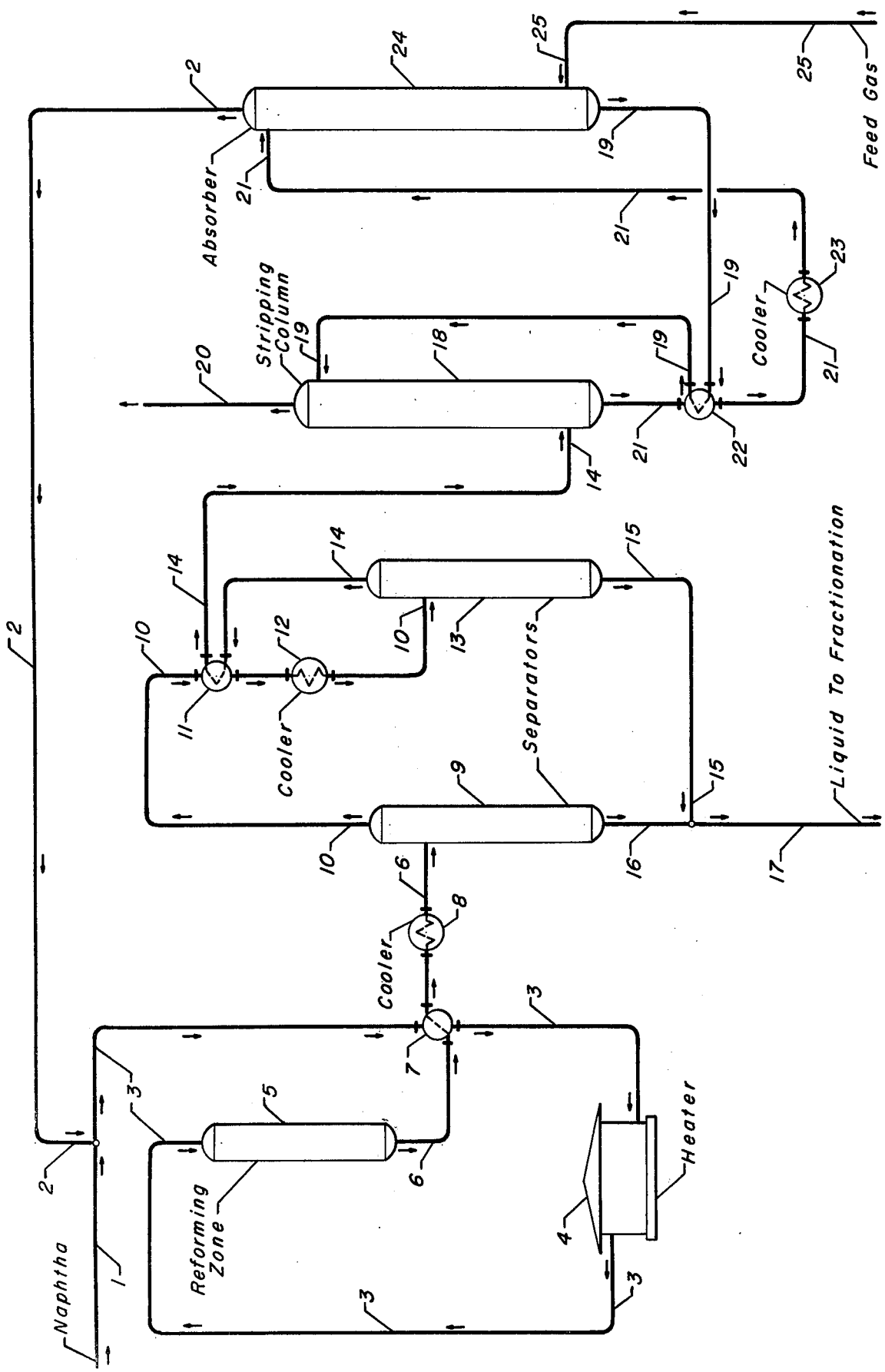

HYDROCARBON REFORMING PROCESS

CROSS-REFERENCE TO RELATED APPLICATION

This application is a Continuation-In-Part of my prior copending application Ser. No. 706,858 which was filed on July 19, 1976, now U.S. Pat. No. 4,058,452 the teachings of which are incorporated herein by reference.

FIELD OF THE INVENTION

The invention relates to a process for the conversion of mineral oils. More specifically, the invention relates to a process for the catalytic reforming of hydrocarbons such as a naphtha. References concerned with similar subject matter may be found in Class 208, and in other classes.

PRIOR ART

The catalytic reforming of hydrocarbons is widely practiced commercially to produce aromatic hydrocarbons and high octane motor fuel blending components. A general description of the process is presented at page 2 of *Industrial Engineering Chemistry*, Product Research and Development, Vol. 15, No. 1, 1976. Those skilled in the art are therefore conversant in the design, construction and operation of catalytic reforming processes.

Some representative examples of the prior art of catalytic reforming are provided by U.S. Pat. Nos. 3,647,680 and 3,650,944 (Cl. 208-65); 3,821,104 (Cl. 208-93); 3,748,260 (Cl. 208-139); and 3,647,679 (Cl. 208-63). These references are relevant for their showing of representative catalyst compositions, operating conditions and procedures, feedstocks and flow schemes. They differ generally from the subject process by the use of recycle hydrogen and the lack of facilities to bypass heavier components of the hydrogen containing makeup gas around the reaction zone.

The use of once-through hydrogen flow in a reforming process is disclosed in U.S. Pat. No. 3,364,137 (Cl. 208-139).

The subject process bypasses hydrocarbons such as paraffins around the reaction zone in a manner similar to my prior copending application in which a thermal hydrodealkylation process was the preferred embodiment. It therefore seems appropriate to mention the methods in which the prior art in the field of hydrodealkylation addressed the presence of undesired hydrocarbons in the feed gas stream.

U.S. Pat. Nos. 3,284,526 and 3,291,849 present processes for the thermal dealkylation of toluene. These references recognize that charging significant quantities of paraffinic hydrocarbons, such as butane, to the reaction zone is normally undesirable. The former reference deals with this problem by operating within certain temperature and residence time limits during the reactant preheating stage. The latter reference addresses the problem in a more pertinent manner by purifying the feed hydrogen in an absorber using part of the alkylbenzene feed as the lean oil. The resulting rich oil is then passed to an appropriate unit in the refinery for fractionation. This reference differs from the subject process in several ways. One of the most basic differences is that in the subject process the paraffinic hydrocarbons which were removed from the feed gas are rejected into the effluent gas stream. Furthermore, the effluent gas stream is beneficially used in the rich oil stripper as a stripping media. In comparison, no stripper is provided in the reference, and the hydrogen vent gas is shown as being vented without utilization as the stripping media. Other differences reside in the reaction zone effluent separation method which is used and in the preferred absorber oil recycling which eliminates the need to utilize a portion of the feed stream as the lean oil.

BRIEF SUMMARY OF THE INVENTION

The invention provides a process for the catalytic reforming of a naphtha in which light hydrocarbons are removed from a hydrogen-containing feed gas stream which is used on a once-through basis. The paraffinic hydrocarbons are removed from the feed gas stream in an absorber, and then the rich oil from the absorber is regenerated by stripping with the effluent gas of the process. The light hydrocarbons are thereby caused to bypass the reforming zone. The effluent gas is preferably heated for use in stripping by heat exchange in the separatory system which produces the effluent gas stream. This separatory system preferably includes two vapor-liquid separation zones with intermediate cooling. The effluent gas of the separatory system is a cold gas stream produced in the second separation zone.

DESCRIPTION OF THE DRAWING

The Drawing illustrates the preferred embodiment of the invention. For simplicity and clarity a large number of pieces of apparatus normally required to operate the process have not been shown. This apparatus includes pumps, compressors, pressure and temperature control systems, reactor and fractionator internals, etc., which may be of customary design. This depiction of the preferred embodiment is not intended to exclude from the inventive concept other embodiments set out herein or which are the result of normal and reasonable modification.

Referring now to the Drawing, a naphtha feed stream which enters the process in line 1 is admixed with a hydrogen-rich gas stream from line 2. The resultant reforming zone feed stream is passed through a heat exchanger 7 and a heater 4 by way of line 3 to raise its temperature to that desired for charging to a reforming zone 5. The effluent of the reforming zone, which preferably is a vapor but may be a mixed phase stream, is transported by line 6 through the heat exchanger 7 and a cooler 8.

The reforming zone effluent stream is then passed into a first vapor-liquid separator 9 as a mixed phase stream. This separator is operated at conditions which promote an efficient division of the reaction zone effluent stream into a first separation zone gas stream removed in line 10 and a first condensate stream removed in line 16. The first separation zone gas stream is cooled in heat exchanger 11 and cooler 12. This forms a mixed phase stream which is passed into a second vapor-liquid separator 13. The conditions maintained within this separator effect the separation of the entering mixed phase stream into a second condensate stream removed in line 15 and a second separation zone gas stream removed in line 14. The first and the second condensate streams are combined and passed to a fractionation zone or other product recovery zone through line 17.

The second separation zone gas stream which comprises hydrogen and light hydrocarbons is heated in heat exchanger 11. It is then passed into the bottom of a trayed stripping column 18 to serve as a stripping media. Additional heat may be supplied to the gas stream by a means not shown. The gas stream rises through the stripper and removes various light hydrocarbons, such as ethane, propane, butane and pentanes, from a rich oil stream fed to the top of the column in line 19. This produces an off gas stream removed from the process in line 20. A lean oil stream is removed from the bottom of the stripping column in line 21 and cooled in heat exchanger 22 and cooler 23. The cold lean oil is then passed into the top of the trayed absorber 24. The lean oil descends the column countercurrent to a rising gas stream and removes from the gas stream the various hydrocarbons which are subsequently released in the stripping column. The feed gas stream enters the bottom of the absorber in line 25, and the portion which remains after absorption is removed in line 2 as the hydrogen-rich gas stream. A rich oil stream containing the absorbed light hydrocarbons is withdrawn from the bottom of the absorber in line 19.

DETAILED DESCRIPTION

In a great many hydrocarbon conversion processes the hydrocarbon being processed is admixed with hydrogen prior to passage through a reaction zone. This is done for such reasons as to aid the vaporization of the hydrocarbon, to provide hydrogen which is necessary for the desired reaction or to prolong the life of the catalyst used in the reaction zone. In many cases the hydrogen is recovered from the reaction zone effluent and recirculated. Often this recycle hydrogen stream is purified before being returned to the reaction zone. However, in a second mode of operation, referred to herein as "once-through" operation, the hydrogen is not recycled, or if recycled it is only after having passed through other processing units or purification steps. This is most commonly practiced in processes which consume only minor amounts of hydrogen or which produce hydrogen. These include isomerization processes, alkylation processes, hydrogenation processes, hydrodealkylation processes and mild desulfurization or denitrification processes. In its broadest embodiment the invention is applicable to these and other processes, in addition to the reforming operation described herein, wherein it is desired to operate with a once-through hydrogen flow.

In its preferred embodiment the invention provides a process for the catalytic reforming of a naphtha. As used herein, the term "naphtha" is intended to refer to a mixture of hydrocarbons including paraffins and aromatics which boils between about 90° F. and 500° F. and preferably between 100° F. and 400° F. It is not required that the naphtha feed stream cover this entire boiling point range, and it may be what is referred to in the art as either a light or a heavy naphtha. The reforming operation may be performed to produce a high octane blending component for motor fuel production. The reforming process may also be used to form an aromatic hydrocarbon-rich feed stream to be charged to an aromatic hydrocarbon separation zone. Such a zone may utilize a selective solvent to recover various aromatics, such as benzene and xylenes, for use in petrochemical processes including the production of plastics or detergents.

In many instances of once-through hydrogen flow reforming, it may be necessary or desirable to purify the hydrogen-containing gas stream which is fed to the process. This could be to provide a high purity hydrogen stream as is used in the process described in previously referred to U.S. Pat. No. 3,364,137. Purifying the gas stream may also reduce the quantity of gas which must be compressed and circulated to maintain a desired hydrogen circulation rate. It may also be desired to remove hydrocarbons which have a tendency to crack into smaller, less valuable compounds in the heater or the reaction zone or which may form coke deposits when exposed to high temperatures. Reducing the volume of the gases in the reaction zone effluent stream may also allow a reduction in size, and therefore cost of the lines and vessels forming the vapor-liquid separation zone. A reduction in the volume of the gas fed to the reaction zone also reduces the duty placed on the heater and thereby reduces the utility costs of operating the process.

It is therefore an objective of the invention to provide a catalytic reforming process utilizing once-through hydrogen flow. It is a further objective of the invention to provide a process for reforming a naphtha using once-through hydrogen flow in which the concentration of $C_2$ to $C_5$ hydrocarbons in the feed gas stream is reduced before the feed gas stream is passed into the reforming zone.

These and other objectives are achieved by operation in a manner similar to the preferred embodiment of the invention or the other embodiments described herein. The preferred embodiment of the invention may be characterized as a catalytic reforming process which comprises the steps of passing a feed gas stream comprising hydrogen and $C_2$ to $C_4$ paraffins through an absorption zone operated under conditions effective to remove $C_2$ to $C_4$ paraffins, including countercurrent contact with a stripping zone liquid effluent stream, and thereby forming a hydrogen-rich gas stream and an absorption zone liquid effluent stream; passing the absorption zone liquid effluent stream into a stripping zone operated at conditions effective to cause the removal of $C_2$ to $C_4$ paraffins from the absorption zone liquid stream, including countercurrent contact with a gaseous stripping media, and thereby forming the stripping zone liquid effluent stream and an off-gas stream comprising hydrogen and $C_2$ to $C_4$ paraffins; admixing the hydrogen-rich gas stream with a naphtha feed stream to form a reforming zone feed stream; passing the reforming zone feed stream through a reforming zone and thereby forming a reforming zone effluent stream; cooling and effecting a partial condensation of the reforming zone effluent stream and passing the reforming zone effluent stream into a first vapor-liquid separation zone operated at conditions effective to form a first condensate stream and a first separation zone gas stream; passing the first condensate stream into a product recovery zone; cooling and then passing the first separation zone gas stream into a second vapor-liquid separation zone operated at conditions effective to form a second condensate stream and a second separation zone gas stream; and, heating the second separation zone gas stream by indirect heat exchange against the first separation zone gas stream and passing the second separation zone gas stream into a lower portion of the stripping zone as the gaseous stripping media.

The specific hydrocarbons which are bypassed around the reforming zone will depend on the composition of the feed gas stream. They may be a mixture of $C_2$ to $C_4$ paraffins as in the preferred embodiment. Alternatively, they may be other types of hydrocarbons, a single hydrocarbon or hydrocarbons having more than four carbon atoms per molecule. In a broad embodiment of the invention, a $C_2$ to $C_6$ hydrocarbon is bypassed around the reforming zone. As in the typical absorption operation, the removal of the bypassed material will not be complete and a portion of the undesired $C_2$ to $C_6$ hydrocarbon content of the feed gas stream will remain in the gas stream which is fed to the reforming zone.

Effective conditions for the operation of the stripping zone and the absorption zone may be selected by those skilled in the art. Optimum conditions will depend on such factors as the composition of the feed gas stream, the liquid chosen for use as the absorption media and the degree of purification of the feed gas stream which is desired. A general range of conditions for the stripping zone include a pressure of from atmospheric to about 400 psig. or higher and a temperature of from about 100° F. to about 500° F. The absorption zone will be operated at a higher pressure or lower temperature or both in order to promote the absorption of the light hydrocarbons. The pressure utilized in this zone may range from about 100 psig. to 1000 psig. or higher, and the temperature may range from about 30° F. or lower to approximately 400° F. It is preferred that both zones comprise a single sieve tray contacting column, but any other suitable apparatus may also be employed. The preferred absorption media comprises a mixture of $C_9$-plus aromatic hydrocarbons, but any material suitable for use as a lean oil and which is readily available may be utilized.

Conditions for use in the first and second vapor-liquid separation zones will also be dependent on variable factors, such as the composition of the material being processed. It is within the expertise of those skilled in the art to select a proper set of conditions. These may be any combination of temperature, pressure and flow rate which produces an effective separation of the reaction zone effluent stream into a gaseous stream and a liquid stream of the desired hydrocarbon product. A broad range of conditions include a temperature of from about 20° F. to 300° F. or higher and a pressure of about 100 psig. to about 1500 psig. Preferably, the second separation zone is operated at a pressure which is only slightly below that utilized in the first separation zone. This allows use of the pressure differential to cause the flow of the process streams without greatly interfering with the second separation operation. The second separation zone is therefore preferably operated at a pressure within about 25 psi. of the first separation zone. The temperature of the second separation is preferably 40° to 100° F. below that used in the first separation zone. The construction of the separation zones, as well as the absorption and stripping zones, may be chosen by those skilled in the art from suitable customary designs.

The use of two vapor-liquid separation zones which are integrated as shown in the Drawing is preferred. However, the invention may be practiced with only a single vapor-liquid separation zone. The conditions used in such a system are preferably the same as those which are preferred for use in the second vapor-liquid separation zone as set out above. The overriding criteria is the production of a vapor stream suitable for use as a stripping media.

Reforming is typically performed at a temperature of from about 550° F. to about 1000° F., and preferably from 700° F. to 900° F. As used herein, the term "naphtha" is intended to refer to a mixture of hydrocarbons, including some aromatic hydrocarbons, which has a boiling point range from 90° F. to 500° F., and preferably between 100° F. and 400° F. This process involves the vapor phase contacting of the feed material with a catalyst containing a platinum group metal in either a fixed bed or a moving bed reactor. The type of reaction zone employed may change the ranges of preferred conditions. For instance, a typical hydrogen to hydrocarbon mole ratio is about 10:1 with a fixed bed operation, but may vary from about 0.5:1 to 20:1. With a moving bed operation the catalyst is subject to frequent regeneration and lower hydrogen to hydrocarbon ratios of from 1:1 to 5:1 may be employed. The pressure utilized within the reforming reaction zone may vary from about 25 psig. to 1000 psig. or higher, but is preferably kept within the range of 50 psig. to about 200 psig. Generally, the liquid hourly space velocity may be from 0.5 to 10, with from 1.0 to 5.0 being a preferred range.

Reforming catalysts vary widely in their composition and in their method of manufacture but almost universally contain one or more platinum group metals in an amount of from about 0.01 to 5 wt.% of the composite, with from about 0.10 to 0.80 wt.% being preferred. The preferred metal is platinum, but palladium, rhodium, ruthenium, etc. may also be employed. This metal is carried on an inorganic oxide support, which is preferably alumina spheres having a diameter of from about 1/16-inch to about ⅛-inch. The catalyst will preferably also contain a combined halogen such as chlorine, fluorine or iodine to impart a desired acid-acting character to the catalyst. This component is suitably present in the range of from about 0.5 to about 1.5 wt.% of the composite when measured as the elemental halogen. The catalyst can also contain a promoter component. Typical promoters are rhenium, germanium, tin, lead and technetium. If used, this component is preferably present in an amount of from 0.1 to about 3.0 wt.% of the catalyst when measured as the elemental metal. The subject invention is not centered on the composition of the catalyst used and suitable catalysts are available commercially. Further details of the reforming of hydrocarbons may be obtained by reference to U.S. Pat. Nos. 3,647,680; 3,821,104; 3,650,944; 3,830,727 and 3,647,679.

I claim as my invention:

1. A process for catalytically reforming a naphtha which comprises the steps of:
    (a) passing a feed gas stream comprising hydrogen and a $C_2$ to $C_6$ hydrocarbon through an absorption zone operated under conditions effective to remove the $C_2$ to $C_6$ hydrocarbon, including countercurrent contact with a stripping zone liquid effluent stream, and thereby forming a hydrogen-rich gas stream and an absorption zone liquid effluent stream;
    (b) passing the absorption zone liquid effluent stream into a stripping zone operated at conditions effective to cause the removal of the $C_2$ to $C_6$ hydrocarbon from the absorption zone liquid effluent stream, including countercurrent contact with a gaseous stripping media, and thereby forming the stripping zone liquid effluent stream and an off-gas stream comprising hydrogen and the $C_2$ to $C_6$ hydrocarbons;
    (c) admixing the hydrogen-rich gas stream with a naphtha feed stream to form a reforming zone feed stream;
    (d) passing the reforming zone feed stream through a reforming zone and thereby forming a reforming zone effluent stream;
    (e) cooling and effecting a partial condensation of the reforming zone effluent stream and passing the reforming zone effluent stream into a vapor-liquid separation zone operated at conditions effective to form a condensate stream and a separation zone gas stream;
(f) passing the condensate stream to a product recovery zone; and,
(g) passing the separation zone gas stream into a lower portion of the stripping zone as the gaseous stripping media.

2. A process for catalytically reforming a naphtha which comprises the steps of:
(a) passing a feed gas stream comprising hydrogen and $C_2$ to $C_4$ paraffins through an absorption zone operated under conditions effective to remove $C_2$ to $C_4$ paraffins, including countercurrent contact with a stripping zone liquid effluent stream, and thereby forming a hydrogen-rich gas stream and an absorption zone liquid effluent stream;
(b) passing the absorption zone liquid effluent stream into a stripping zone operated at conditions effective to cause the removal of $C_2$ to $C_4$ paraffins from the absorption zone liquid effluent stream, including countercurrent contact with a gaseous stripping media, and thereby forming the stripping zone liquid effluent stream and an off-gas stream comprising hydrogen and $C_2$ to $C_4$ paraffins;
(c) admixing the hydrogen-rich gas stream with a naphtha feed stream to form a reforming zone feed stream;
(d) passing the reforming zone feed stream through a reforming zone as a vapor and thereby forming a reforming zone effluent stream;
(e) cooling and effecting a partial condensation of the reforming zone effluent stream and passing the reforming zone effluent stream into a first vapor-liquid separation zone operated at conditions effective to form a first condensate stream and a first separation zone gas stream;
(f) passing the first condensate stream to a product recovery zone;
(g) cooling and then passing the first separation zone gas stream into a second vapor-liquid separation zone operated at conditions effective to form a second condensate stream and a second separation zone gas stream; and,
(h) heating the second separation zone gas stream by indirect heat exchange against the first separation zone gas stream and passing the second separation zone gas stream into a lower portion of the stripping zone as the gaseous stripping media.

* * * * *